(12) United States Patent
Geurts et al.

(10) Patent No.: US 10,426,971 B2
(45) Date of Patent: Oct. 1, 2019

(54) PHOTOTHERAPY DEVICE WITH PAIN LOCATION INPUT

(71) Applicant: KONINKLIJKE PHILIPS N.V., Eindhoven (NL)

(72) Inventors: Lucas Jacobus Franciscus Geurts, Best (NL); Vincentius Paulus Buil, Gennup (NL); Maria Estrella Mena Benito, Eindhoven (NL); Ramon Eugene Franciscus Van De Ven, Eindhoven (NL); Peter Bingley, Mierlo (NL); Adam Henriksson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/316,872

(22) PCT Filed: May 19, 2015

(86) PCT No.: PCT/EP2015/060993
§ 371 (c)(1),
(2) Date: Dec. 7, 2016

(87) PCT Pub. No.: WO2015/189008
PCT Pub. Date: Dec. 17, 2015

(65) Prior Publication Data
US 2017/0113063 A1    Apr. 27, 2017

(30) Foreign Application Priority Data

Jun. 11, 2014 (EP) ..................... 14171982

(51) Int. Cl.
*A61N 5/06* (2006.01)

(52) U.S. Cl.
CPC .... *A61N 5/0622* (2013.01); *A61N 2005/0626* (2013.01); *A61N 2005/0645* (2013.01);
(Continued)

(58) Field of Classification Search
CPC .......... A61N 5/0622; A61N 2005/0626; A61N 2005/0645; A61N 2005/0652; A61N 2005/0662
(Continued)

(56) References Cited

U.S. PATENT DOCUMENTS

2001/0008973 A1   7/2001  Van Zuylen et al.
2007/0233208 A1  10/2007  Kurtz et al.
(Continued)

FOREIGN PATENT DOCUMENTS

CN  102805707 A  12/2012
CN  203483578 U   3/2014
(Continued)

*Primary Examiner* — Aaron F Roane (57) ABSTRACT

A phototherapy device with pain location input phototherapy device for relieving nociceptive pain of a body part of a user by illumination of at least a part of the body part. A controllable light source system (LS1, LS2, LS3) comprises at least one light source arranged on a patch structure (PS) so as to allow phototherapeutic illumination of a body part. A user interface (U_I), e.g. a touch panel (TP), is arranged to receive an input from the user regarding a spatial position on the body where the user feels pain. A control system (CS) is arranged to control the controllable light source system (LS1, LS2, LS3) in accordance with said input from the user, e.g. to spatially intensify illumination at the position where the user indicates a sensation of pain. E.g. the device may be wirelessly controlled from the a smart phone, where a map of the body can be displayed, and where the user indicates on this map where he/she feels pain.

11 Claims, 3 Drawing Sheets

(52) U.S. Cl.
CPC ............ *A61N 2005/0652* (2013.01); *A61N 2005/0662* (2013.01); *A61N 2005/0663* (2013.01)

(58) Field of Classification Search
USPC .......................................................... 607/88
See application file for complete search history.

(56) References Cited

U.S. PATENT DOCUMENTS

| | | |
|---|---|---|
| 2010/0234927 A1 | 9/2010 | Lin |
| 2011/0218597 A1 | 9/2011 | Wang |
| 2011/0263950 A1 | 10/2011 | Larson et al. |
| 2012/0197358 A1* | 8/2012 | Prescott ............... A61N 5/0613 607/89 |
| 2012/0303100 A1 | 11/2012 | Pryor et al. |
| 2013/0137992 A1 | 5/2013 | Yamazaki et al. |

FOREIGN PATENT DOCUMENTS

| | | |
|---|---|---|
| EP | 2540345 A1 | 1/2013 |
| JP | 2002078772 A | 3/2002 |
| JP | 2007020949 A | 2/2007 |
| JP | 2012514498 A | 6/2012 |
| KR | 2011132101 A | 12/2011 |
| RU | 2006129892 A | 2/2008 |
| WO | 2009024923 A2 | 2/2009 |
| WO | 2010011024 A2 | 1/2010 |
| WO | 2010078581 A1 | 7/2010 |
| WO | 2014024092 A1 | 2/2014 |

\* cited by examiner

PHOTOTHERAPY DEVICE WITH PAIN LOCATION INPUT

CROSS-REFERENCE TO PRIOR APPLICATIONS

This application is the U.S. National Phase application under 35 U.S.C. § 371 of International Application No. PCT/EP2015/060993, filed on May 19, 2015, which claims the benefit of European Patent Application No. 14171982.3, filed on Jun. 11, 2014. These applications are hereby incorporated by reference herein.

FIELD OF THE INVENTION

The present invention relates to the field of devices for relieving nociceptive pain of a body part of a user. More specifically, the invention provides a photography device with an input for the user to indicate a position or location of pain, and wherein the device generates phototherapy accordingly.

BACKGROUND OF THE INVENTION

Pain is a sensory experience that may be described as the unpleasant awareness of a noxious stimulus or bodily harm. According to the International Association for the Study of Pain (IASP), pain is defined as an unpleasant sensory and emotional experience associated with actual or potential tissue damage or described in terms of such damage. Industry analysts estimate that more than 1.5 billion people around the world suffer from chronic pain, making it the number one reason patients seek medical care. Muscle pain in the shoulder-neck area or the upper or lower back is a very common problem.

Pain is a personal, subjective, multi-faceted construct under the influence of cultural learning and having physiological as well as (emotional and non-emotional) psychological elements. It is therefore inherently difficult if not impossible to assess in a truly objective manner because, on the one hand, two patients with identical physiological symptoms may experience their pain completely different due to differences in their sensitivity to pain or habituation to pain from earlier experiences.

Many techniques for pain treatment exist such as medication and physical exercises. Other solutions use heat and light therapy (e.g. Infra Red lamps). Increased temperature will stimulate thermal receptors in deep tissue. The thermal signal that the body generates then inhibits transmission of nociceptive signals. In addition, it causes physiological responses such as increased blood flow and metabolism, and is reported to relax muscles by decreasing the alpha motor activity from the dorsal horn.

An example of a phototherapy device is developed by Philips and has the form of an electronic patch designed to strip around the user's body for muscular backache. The patch has an array of blue Light Emitting Diodes (LEDs) in its inner part which can be switched on so as to deliver phototherapeutic blue light to an area of the skin of the user's body. A user can fasten the patch around his/her body using an elastic band, and thus the user can walk around with the patch kept in place, while receiving phototherapy.

SUMMARY OF THE INVENTION

It would be advantageous to provide a phototherapy device which has an improved pain relieving effect on an individual person's sensation of pain. Further, it would be advantageous that such device is capable of saving electric power. Still further, it would be advantageous to be able to provide a higher intensity of phototherapeutic light.

In a first aspect, the invention provides a phototherapy device for relieving nociceptive pain of a body part of a user by illumination of at least a part of the body part, wherein the device comprises
  a patch structure arranged to conform with at least a part of the body part,
  a controllable light source system comprising at least one light source arranged on the patch structure so as to allow phototherapeutic illumination of at least a part of the user's body part, when the patch structure is positioned on the body part,
  a user interface arranged to receive an input from the user regarding a spatial position on the body, and
  a control system arranged to control the controllable light source system in accordance with said input from the user, wherein the user interface further comprises a touch sensitive panel arranged on the patch structure, the touch sensitive panel arranged on the opposite side to the side confirming with the at least a part of the body part.

Such device is advantageous since the user interface allows the user to indicate the exact position on the body where the user feels pain, and the control system can then spatially direct the phototherapy illumination to the spatial position on the body indicated by the user. Thereby, phototherapeutic illumination is applied to the part of the body where the user feels pain, or to a part of the body which is found, based on physiological knowledge, to be beneficial to apply phototherapeutic illumination to for optimal effect in view of the spatial position on the body where the user indicates the feeling of pain. Thus, it is possible to individualize the phototherapy to the user's need and thus increase the phototherapeutic effect. It is possible to manufacture one generic controllable light source system and patch structure which can cover a large body area, and still it is possible for the user to spatially pinpoint the location of pain and receive nociceptive pain relieving phototherapy only where it is required.

The user interface comprises a touch sensitive panel arranged to sense touch by the user at spatially different locations. Especially, the touch sensitive panel may be arranged on an opposite side of the patch structure as the at least one light source. Hereby, the user can indicate a position of pain while wearing the patch, i.e. having fastened the patch to a body part, e.g. the back or the shoulder-neck region, and by touching the painful position or area(s) on top of the patch, the touch panel is arranged to sense the painful area. This is an easy way of indicating a painful area for the user, since he/she merely has to directly touch the painful area with his/her hand(s). The touch sensitive panel may comprise at least one of: an acoustic touch panel, an optical sensor panel, a swept frequency capacitive sensor panel, and a nano-touch sensor panel. I.e. in general, the touch panel may use one of a range of technologies as known by the skilled person.

The fact that the illumination can be controlled so as to be spatially limited to only the area required by the user, helps to save battery power compared to phototherapy device which can not spatially control its light sources. This allows use of a smaller battery, and/or allows longer duration of treatment without the need for recharging the battery. Both are beneficial for patient with chronic pain which requires the patient to wear the phototherapy for long periods, e.g.

each day. Still further, by illuminating only a spatially limited area where the user feels pain means that the intensity can be increased at this limited area without excessive heat being produced, and still only with the battery power required to illuminate the painful area.

The invention is based on the insight that improved phototherapy can be obtained, i.e. improved pain relieving effect can be obtained, in case the phototherapy is adapted to the individual need of the user. Still further, even for an individual user, the sensation of pain may change during a day, both with respect to intensity, but also perceived spatial location. With the device according to the first aspect, this can be taken into account and thus improve the pain relieving effect for the user.

In preferred embodiments, the light source comprises blue light Light Emitting Diodes (LEDs), i.e. LEDs capable of providing light with a wavelength within the range 430-480 nm. Especially, and it has recently been verified that such blue light can provide an improved pain relieving effect on muscular pain by using pulsating light instead of continuous light, since it is possible to increase the penetration depth of light into the tissued without increasing the thermal load. Thus, various parameters of such pulsating light can also be controlled by the user interface, e.g. allowing the user to indicate intensity of pain. E.g. light intensity and/or light pulsating frequency can be adapted to the user input.

In the following a number of embodiments and features with be described.

The control system may be arranged to control the phototherapeutic illumination from the controllable light source system in accordance with said input from the user, so as to spatially adapt the phototherapeutic illumination to the spatial position on the body input by the user. Thus, the user can input a position of pain on his/her body, and the phototherapeutic illumination is then directed to the position where the user feels pain, thereby allowing the device to adapt to the user's individual need. Hereby electric (battery) power can be saved, since only a part of the available light sources needs to be activated, and further no unnecessary heat will be generated, since the device can be adapted to provide therapeutic illumination only to the painful position or area.

The control system may be arranged to control the controllable light source system so as to change at least one parameter of the phototherapeutic illumination in response to the spatial position on the body input by the user. Especially, said at least one parameter may comprise at least one of: illumination light duration, illumination light intensity, illumination light wavelength, illumination light pulsation width, and illumination light pulsation frequency. Also any combination of these could be used: patterns of changing intensities, wavelengths, pulsation, with patterns of multiple LEDs each behaving differently at the same time (e.g. animations on matrix displays). Furthermore, cycled execution of a certain pattern may be used (e.g. on-off-on-off with specific durations). Still further, two or more points indicated by the user could be used, e.g. to alternate the treatment between these two or more points. Alternatively, the user can make a gesture or stroke to indicate an area or direction of the pain. The program/sequence could take this into account when making a pain treatment program. Thus, with the spatial position input from the user, the device can control the applied light in different ways, e.g. intensify illumination and/or illumination light pulsation frequency, in the body position or area(s) indicated as painful by the user. Alternatively, the control system may be arranged to only switch on light source(s) positioned at the body position or area(s) which the user has indicated as painful.

The input from the user may be processed in accordance with a control algorithm, so as to translate the input from the user into a spatial illumination pattern, and wherein the control system is arranged to spatially control the controllable light source system accordingly. Especially, the control algorithm may translate the input from the user into the spatial illumination pattern in response to prestored physiological information. This allows an intelligent processing of the painful position or area(s) indicated by the user, since it may be taken into account that certain painful sensations can most efficiently be treated by illumination of a body area which is different from the position or area(s) indicated by the user, e.g. by recognizing the input by the user as one of a number of normally occurring pain sensations, and in response activating a prestored illumination accordingly.

The user interface may be arranged to allow a user to enter an indication of pain intensity, and to adapt at least one parameter of the phototherapeutic illumination in response thereto. Especially, illumination light duration, illumination light intensity, illumination light wavelength, illumination light pulsation width, and illumination light pulsation frequency may be adapted in response to a pain intensity indicated by a user. Especially, the user interface may be arranged to allow the user to indicate pain intensity by means of sensing a force applied by the user. Such as by using a force sensor as known in the art, e.g. the force sensor may be arranged to sense force at the same time as indicating the painful position. Alternatively, the user interface may be arranged for indication of a pain intensity by means of entering a number, by turning a knob etc.

The controllable light source system may comprise a plurality of individually controllable light sources arranged at respective spatially different zones relative to the patch structure. Especially, the control system may be arranged to activate a limited number of the individually controllable light sources in response to the input from the user, so as allow phototherapeutic illumination for nociceptive pain relief of the body part where the user feels pain. Hereby an optimal pain relief effect can be obtained and at the same time electric power can be saved, thus allowing e.g. more light intensity or light with a higher pulsation may be used at the same electric power consumption as prior art devices where all light sources are active at all times. More specifically, the controllable light source system may comprise a plurality of spatially separated individually controllable light source groups each comprising a plurality of single light sources.

In another group of embodiments of the device, the user interface comprises a camera system arranged to recognize a spatial position or body part which the user indicates, e.g. a spatial position which the user indicates by his/her hand. Thus, such system preferably comprises a camera, and an image processing algorithm arranged to determine, in response to one or more image from the camera, which spatial position or body part the user indicates.

In still another group of embodiments of the device, the user interface may comprise a control device separate from the patch structure, wherein the control device is arranged for the user to operate in order to indicate said spatial position on the body, e.g. a position where pain is felt. This separate control device can be implemented in a large variety of ways. Especially, the control device may comprise at least one of: a control stick, a computer mouse, a track ball, a set of buttons, a touch pad, and a touch screen. In a special embodiment, the control device comprises a physical doll that is touch sensitive, as a representation of the user's own body, where pain treatment will be done at the user's body part where the user lays his hand on the doll's body. To help facilitate the indication of the spatial position on the body, the user interface may be arranged to display a map of at least a part of a body on which the user can indicate a position of pain.

In yet another group of embodiments of the device, the user interface is arranged to receive the user input from an external device, e.g. said external device being one of: a smart phone, a tablet, and a personal computer. Especially, the user interface is arranged to receive data indicative of the spatial position on the body which the user has entered on the external device. Specifically, the user interface may be arranged to receive such data by means of a wireless connection to the external device, such as by means of a Near Field Communication (NFC) standard, Bluetooth etc. In a specific embodiment, the device has a wireless receiver arranged near the patch, e.g. mounted as a part of the patch structure, and being arranged to receive data indicative of the spatial position on the body which the user has entered on the external device in a wireless form. Further, the device comprises an application program for the external device, e.g. a smart phone, which allows the user to indicate said spatial position on the body on the external device, which then wirelessly transmits data indicative therof to the wireless receiver.

The controllable light source system preferably comprise at least one light source arranged to provide light with at least one wavelength within the range 430-480 nm, i.e. blue light which has been verified to provide a pain relieving effect. Especially, the controllable light source system may comprise a plurality of LEDs. E.g. such as a number of LEDs spatially arranged in a 2D array covering an area of more than 10×10 cm.

The device may comprise a fastening structure so as to allow the user to fasten the patch structure to the body part. The patch structure may be made of a flexible material allowing the patch to conform with different shapes of body parts.

In a specific embodiment, the phototherapy device comprises a plurality of blue light LEDs spatially spread to cover a zone or area. A processor, a battery for powering at least the processor and the LEDs, and a control panel allowing the user to indicate a pain position, are all mounted together with the patch structure. The patch structure is preferably sized and shaped to fit to be worn by the user on his/her back, shoulder, or on a limb. Preferably, the phototherapy device has a fastening element serving to allow fastening to the user's body part.

The device preferably comprises a battery, such as a rechargeable battery, arranged to provide all electric power necessary or powering the device. This allows the user to wear the device and walk around without the need for wiring to electric power. Further, the invention has the potential to save electric power, and thus allows the use of a smaller battery or allows longer duration of phototherapy with a given battery capacity.

In a second aspect, the invention provides a product comprising a phototherapy device according to the first aspect. In such product, at least the patch structure and the at least one light source may be mounted on or in an additional device. E.g. in a manner such that the phototherapy device forms an integral part of, or constitutes one single unit together with the additional device. Especially, the additional device may be: a piece of clothes, a piece of furniture, e.g. a massage chair, a wheel chair, and a medical therapeutic device. Still further, the additional device may comprise a driver or passenger chair in a car, a bus, a train, a plane, a boat, a hospital bed, a worn baby carrier, a backpack, or a belt on large worn musical instruments (tuba, accordion, etc.), or any wrist worn devices such as watches, bracelets, etc. Even further, the additional device may comprise undergarment or underwear, e.g. a bra.

In a third aspect, the invention provides a method for controlling a phototherapy device for relieving nociceptive pain of a body part of a user by illumination of at least a part of the body part, wherein the device comprises a patch structure arranged to conform with at least a part of the body part, and at least one light source arranged on the patch structure, the method comprising
  receiving an input from the user regarding a spatial position on the body, and
  controlling at least one light source arranged on the patch structure in accordance with the input from the user.

Such method can be implemented as a computer executable program code capable of performing the steps of the method according to the third aspect. Thus, the method can be in software, e.g. as an add-on or modification of existing software in a phototherapy device. The computer executable program code may especially be present on a non-transitory computer readable storage medium, or it may be loaded into memory of a processor system arranged to execute the program code.

In a fourth aspect, the invention provides a computer executable program code adapted to cause an external device, e.g. a mobile device, such as a smart phone:
  to receive an input from a user regarding a spatial position on the body, and
  to control at least one light source arranged on the patch structure of the phototherapy device according to the first aspect, in accordance with the input from the user. The program may cause the mobile device to display a map of the human body, and to allow the user to enter a position or an area on the human body as input regarding a spatial position on the body where the user feels pain. Alternatively, a camera in the external device may be used by the user to take a photo of the painful area as an indication of the spatial position on the body. The external device is preferably capable of transmitting wireless data to the phototherapy device in order to control the controllable light source system according to the user input. In a further option, a therapist may be able to set a program or treatment of the device, which may then be triggered later by the user when he/she feels pain.

It is appreciated that the same advantages and embodiments of the first aspect apply as well for the second, third, and fourth aspects. In general the first, second, third, and fourth aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
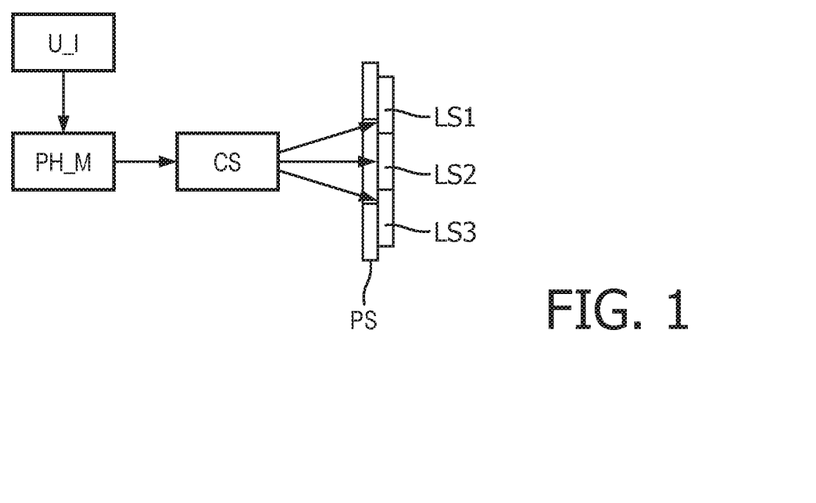
FIG. 1 illustrates a block diagram of one embodiment.

FIG. 1 illustrates basic parts of a block diagram of a phototherapy device embodiment for relieving nociceptive pain of a body part of a user. In this embodiment, a controllable light source system comprises three groups of spatially differently positioned light sources LS1, LS2, LS3, preferably each comprising a plurality of blue light LEDs, e.g. arranged in arrays to each cover a certain area or zone. Such blue light LEDs are proven to provide a nociceptive pain relieving effect by illumination of a part of a user's body when illuminating the skin of the body part. The light sourcer of the light source groups LS1, LS2, LS3 are arranged on a patch structure PS, e.g. a flexible material, such as a woven, anon-woven, a polymeric material, which is arranged to conform with at least a part of the body part, e.g. the back of a person. Thus, when the patch structure PS is positioned on the body part of the user, the light source can provide phototherapeutic illumination of the body part.

A user interface U_I serves to receive an input from the user regarding a spatial position on the body. This can be done in a variety of ways, e.g. via an external device, such as a smart phone, or using a touch panel mounted on the back side of the patch structure, thus allowing the user to indicate the relevant position on the body by touching the body part, when the patch structure is fastened to the body part.

A control system CS serves to control the controllable light source system LS1, LS2, LS3 in accordance with said input from the user, e.g. by switching on only the group(s) of light sources LS1, LS2, LS3 which are located at the body position indicated by the user as painful. Additionally or alternatively, the control system CS can control the controllable light source system by providing different illumination intensity and/or pulsation frequency to the different light source groups LS1, LS2, LS3 in order to provide the highest amount of phototherapeutic illumination to the body position indicated as painful by the user.

In the illustrated embodiment, the input from the user interface U_I is applied to an algorithm, wherein the indicated pain position is processed according to a physiological model so as to, if necessary, apply light to a different area than indicated by the use, in case the physiological models detects that the pain position indicated is best pain relieved by providing phototherapy to another area than indicated by the user. This may be due to the pain felt at one position is actually caused by nerves or muscles located differently etc. E.g. light may applied to an entire area of a muscle, even though the user indicates a specific point of pain.

Figure 2:
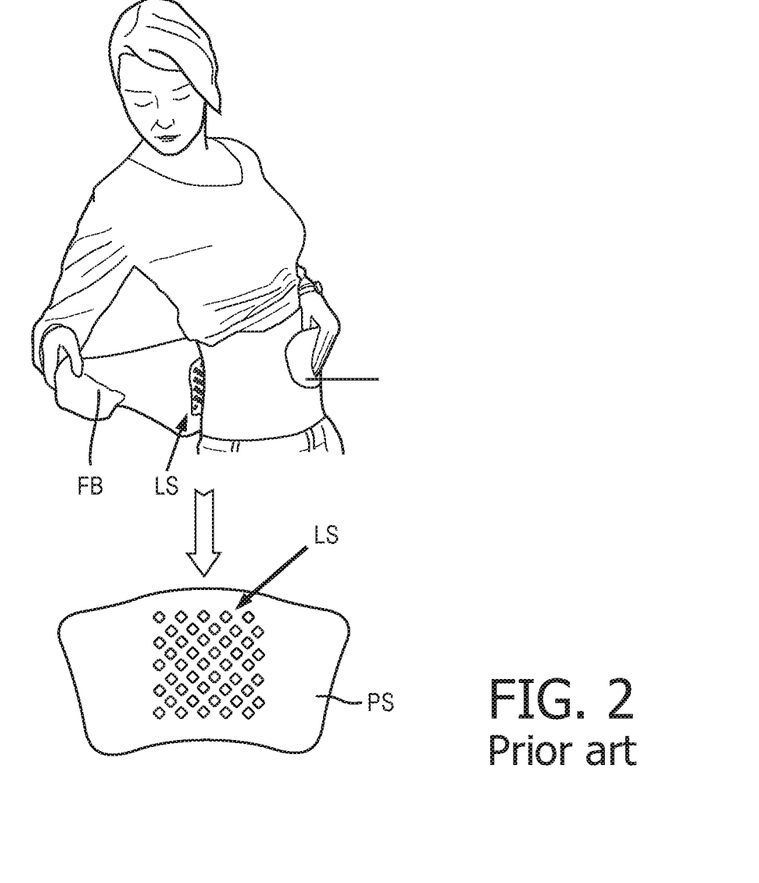
FIG. 2 illustrates photos showing a prior art device with blue light LEDs.

FIG. 2 shows photos of a prior art device with 50 blue light (450 nm wavelength) LEDs arranged on a patch structure PS, and suited for direct contact with the skin of the user. A belt FB allows the user to fasten the device to the body, here illustrated as the lower back. In this prior art device, the user can switch power to the light sources LS "on" or "off".

It is to be understood that the prior art blue light patch shown in FIG. 2 can form the basis for a device according to the invention, provided that it is supplied with a controllable light source system, a control system, and a user interface according to the invention. This allows an intelligent blue light patch device with improved user interaction for individual adaptation to the user's need. A range of sensors will be able to capture information about the (specific) localization of the user's pain, and this information will be consequently transmitted to the control system which will then adapt the (blue) light characteristics at the source (pointed area) of pain. The user interface for recognizing location of the user's pain is preferably able to recognize the touch events of the user. It can be done by using the following systems: a system using touch sensors, a system using camera recognition of touch position, and a system using a controller to indicate the pain position.

Such an intelligent system according to the invention is able to recognize the source of the user's pain (pointed area) and consequently to react to this action by activating the phototherapeutic light system, e.g. adapting the width, frequency or pulse frequency, of (blue) light at the pointing area. Additionally, when the user keeps a point pressed for a longer period of time, or applies more pressure, this may be interpreted as an action to increase the intensity at that area and decrease it where the user does not touch the user interface.

Figure 3A:
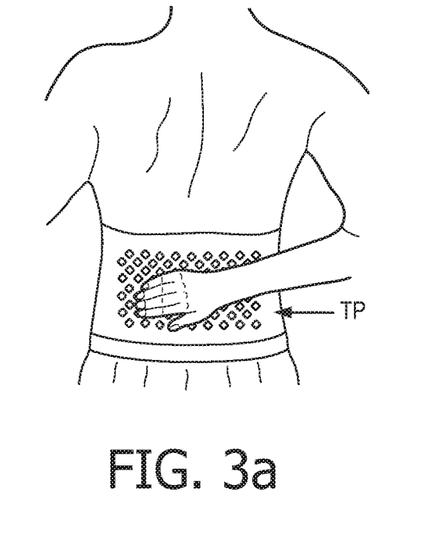
FIGS. 3a and 3b illustrate a photo and a block diagram of a user interface in the form of a touch sensitive panel positioned on one side of the patch structure, opposite the side where light source are positioned.

FIG. 3a shows a user wearing a phototherapy device according to the invention, e.g. with a patch structure similar to the one of the prior art device of FIG. 2, where a user interface comprises a touch panel TP arranged on the opposite side of the patch structure of where the light sources, e.g., blue light LEDs are positioned, and wherein a control system can control the light sources in response to a body position indicated by the user on the touch panel. The device then adapts the phototherapy accordingly, so as to provide light where the user needs it to obtain a good pain relieving effect, e.g., by increasing light at the area indicated by the user. The picture indicates a device used on the lower back of the user; however, it is to be understood that the device could be used also at other parts of the body as well. The touch panel TP may be arranged to sense a force applied by the user, so as to allow the user to indicate an intensity of the pain felt at the body position indicated on the touch panel TP, thus allowing the control system to control the light sources accordingly.

Figure 3B:
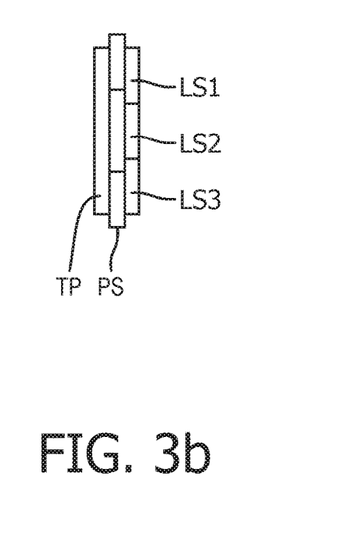

FIG. 3b shows a block diagram of the device of FIG. 3a, where the touch panel TP is seen to be positioned on the opposite side of the patch structure PS. The control system (not shown in FIG. 3b) can respond to the position input from the touch panel TP by adapting the light from one or more of the group of light sources LS1, LS2, LS3 in various ways, so as to adapt the resulting phototherapeutic illumination according to the user's needs. E.g. when the user touches the touch panel TP in the area above where the light source group LS2, the control system may be programmed to switch on only the light source group LS2. However, a variety of more complicated patterns of illumination can be provided, such as already explained.

Various touch panel technologies may be used for the touch panel TP. E.g. an acoustic touch position panel system, where a substrate on top of the patch structure PS contains a surface acoustic panel capable of recognizes and locates the perturbation due to user's touch. The system may comprise also a transducer, responsive to touch perturbed surface wave(s) indicating the position of the touch on the substrate surface. A tactile touch sensor panel and/or a tactile pressure sensor may be used. E.g. a capacitive activated transducer system containing a sensor responsive to human touch by generating a change in frequency of an oscillator output. A swept frequency capacitive (SFC) sensor can be used, e.g. such SFC can be integrated in a substrate on top the patch structure PS. The SFC sensor can detect changes in electrical signal corresponding to a touch event. Nano-touch sensors may also be used. When pressed or touch the solenoid of silicone inside the nano touch pad provides a tactile feedback confirmation, similar to the one produced by a micro switch. No tactile pressure sensors may also be used. An un-obtrusive capacitive sensor system can detect contact from the users hand without requiring pressure or mechanical actuation of a switch, e.g. similar to the ones using in a touch type trackball. Prefarbly, the system comprises a microcontroller for interpreting the signal and inform to the touchpad when is touched (contacted) and when relieved. Optical sensors may also be used. E.g. a diffuse infrared (IR) light sensors, where changes in the diffuse light will indicate if user has touched (positioned on) the surface of the device. Still further, a matrix of X and Y light guides that guide part of the available blue LED light sources to photodiodes on the side of the patch structure PS. When the user presses on the back of the patch structure PS, the light through the corresponding X and Y guides will be interrupted, thus providing the system with the info where the patch was touched. Yet further, a flexible poly LEDs touch sensor may be used, where a touch switch using an optical touch sensor based on polymer light-emitting polymer photodiodes is utilized. The sensor's thin film light sources and detectors are flexible and can be integrated on top of the patch structure PS.

Figure 4:
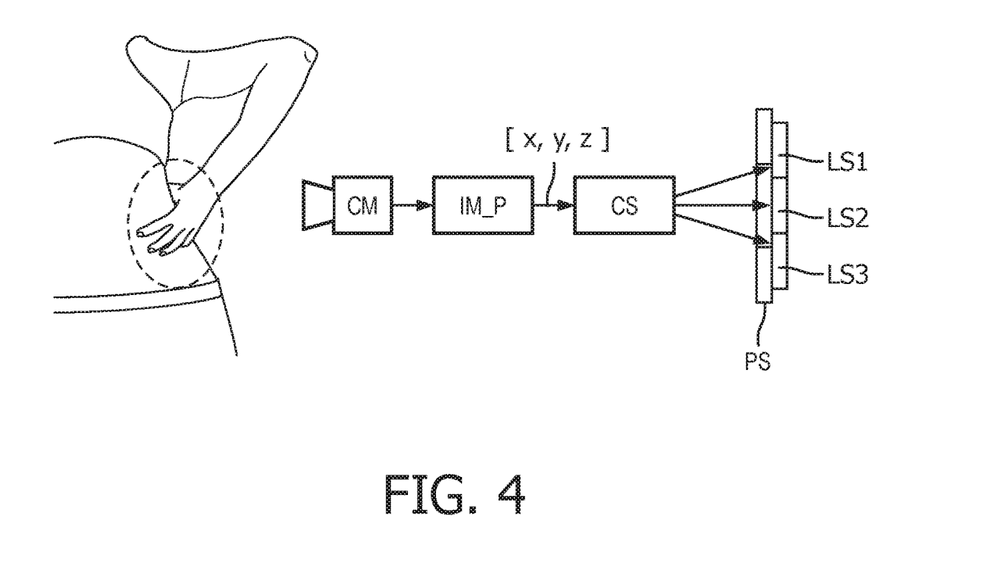
FIG. 4 illustrates an embodiment where the user indicates a location of pain with his/her hand which is registered by the phototherapy by means of a camera.

FIG. 4 shows a photo, to the left, of a user indicating position of pain by her hand (indicated with the dashed area). To the right, a block diagram indicates elements of a device embodiments with light source groups LS1, LS2, LS3, a patch structure PS, and a control system CS, just as explained e.g. in connection with FIG. 1. The user interface in this embodiment comprises a camera CM arranged to provide one or a series of images of the user indicating a position on the body where pain is felt. This or these images from the camera CM are applied to an image processing IM_P algorithm which determines the indicated position on the body accordingly, e.g. as x,y,z coordinates, or as a selection part of of a prestored spatial segmentation of the body. This information is then provided to the control system CS which controls the light source system LS1, LS2, LS3 accordingly, as already explained.

The camera CM used and the image processing IM_P may be provided by a smart phone supplied with a dedicated application program. Thus, the user can take a photo of the painful body part, or indicating with a finger or hand on the body part, and the processed result can then be wirelessly communicated to the control system CS, which can be located in one units together with the patch structure PS and light sources LS1, LS2, LS3. Thus, in essence, in such embodiment, the function of the phototherapy device is controlled from the user's smart phone.

Figure 5:
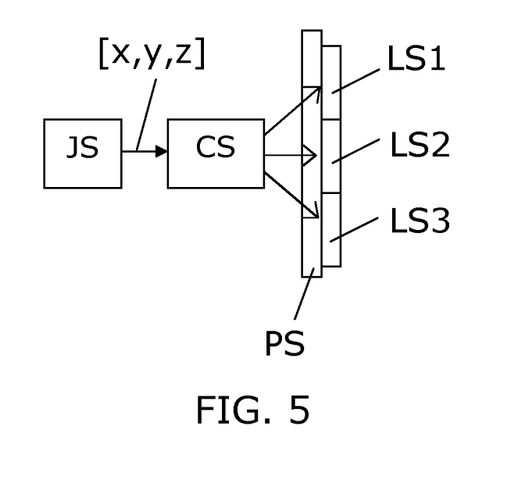
FIG. 5 illustrates a block diagram of an embodiment where the user indicates location of pain by means of a joystick.

FIG. 5 shows a block diagram of an embodiment with the same components as explained above, e.g. in connection with FIG. 1, however in an embodiment where the user interface comprises a controller JS, e.g. a joystick, arranged for the user to indicate the position on the body, and thus to guide the location where lighting characteristics (e.g. intensity and pulse) of the therapeutic (blue) light should be adapted. The coordinates x, y, z indicated by the user are then provided to the control system CS which functions as already explained.

A joystick JS may be used enable the user to communicate with the control system CS. A signal output is generated by the joystick JS. Such joystick JS may comprise a movable control stick with two sensors: a sensor to indicate positions or directions, and a second sensor coupled to the control stick that can adapt the characteristics of the light. Alternatively, the controller JS could be a mouse, a trackball, buttons, touch pad, touch screen or any other controller that is specifically designed for this system, or that is available on a smart phone or tablet. An image of (part of the) body may be displayed where the user can pinpoint the pain location. This information may then be wirelessly sent to the control system, and its behaviour is changed accordingly, e.g. by adapting the intensity and/or frequency of the light at the desired point.

Figure 6:
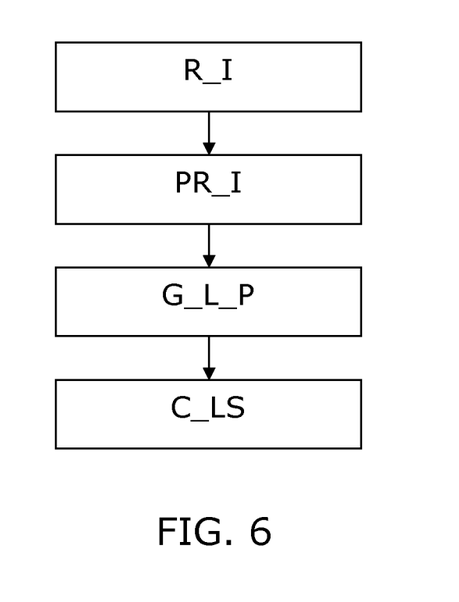
FIG. 6 illustrates a block diagram of steps of a method embodiment.

FIG. 6 illustrates steps of a method embodiment, i.e. a method for controlling a phototherapy device for relieving nociceptive pain of a body part of a user by illumination of at least a part of the body part, wherein the device comprises a patch structure arranged to conform with at least a part of the body part, and at least one light source arranged on the patch structure. In a first step R_I, the method comprises receiving an input from the user regarding a spatial position on the body, e.g. where the user feels pain. In a second step PR_I, this input is processed, so as to determine which part of the body the user feels pain. Based on knowledge on where the patch structure is placed on the user body, the following step G_L_P is to generate a light pattern adapted according to where the user feels pain, and to where the patch is positioned relative to the user's body. Finally, the step of controlling C_L at least one light source arranged on the patch structure in accordance with the generated light pattern is performed.

In the following a number of additional embodiments will be mentioned. E.g. a plurality of capacitive touch pad sensors can be integrated on top of the patch structure. In an additional embodiment, the device may contain an additional touch sensor designed to confirm the touch detected by a first touch sensor and discriminated it from false user's touches. Preferably, such sensors are of different type. If the touch detected by the first touch sensor is not confirmed by the second one, the touch will not be considered valid, and the control system will not take the input into account.

Especially, false touches may be triggered in case of clothing worn over the patch, depending on the touch technology. However, this may be eliminated or reduced by the user interface being configured for processing of input signals to discriminate between hand touches (i.e. desired inputs) from touch from clothing (i.e. undesired inputs).

A memory system can be integrated into the device, so as to remember locations of pain (pointed area) from earlier, which is helpful e.g. in case the user suffers from chronic pain. When using a camera to indicate position of pain, also markers (or tags) could be used that are placed by a person on points where his or her muscles hurt. These markers could be detected by the camera and used e.g. for targeted treatment.

The invention provides a number of advantages. E.g. personalisation and optimisation of the pain relief effect of the phototherapy device. Additionally, it creates relaxation time for the skin, since the shorter the light pulse, the longer the relaxation time. Furthermore, it enhances the penetration depth by delivering the light in irradiance peaks at the source, i.e. pointed area, of pain.

To sum up, the invention provides a phototherapy device with pain location input phototherapy device for relieving nociceptive pain of a body part of a user by illumination of at least a part of the body part. A controllable light source system LS1, LS2, LS3 comprises at least one light source arranged on a patch structure PS so as to allow phototherapeutic illumination of a body part. A user interface U_I, e.g. a touch panel TP, is arranged to receive an input from the user regarding a spatial position on the body where the user feels pain. A control system CS is arranged to control the controllable light source system LS1, LS2, LS3 in accordance with said input from the user, e.g. to spatially intensify illumination at the position where the user indicates a sensation of pain. E.g. the device may be wirelessly controlled from the a smart phone, where a map of the body can be displayed, and where the user indicates on this map where he/she feels pain.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A phototherapy device for relieving nociceptive pain of a body part of a user by illumination of at least a part of the body part, comprising:
   a patch structure arranged to conform to at least a part of the body part;
   a controllable light source system comprising at least one light source arranged on the patch structure so as to allow phototherapeutic illumination of at least a part of the user's body part, when the patch structure is positioned on the body part;
   a user interface having a touch sensitive panel arranged on the opposite side to the side conforming to the at least a part of the body part, wherein the touch sensitive panel is arranged to sense a force applied by an input of the user corresponding to the noicipceptive pain such that the input from the user corresponds to a spatial position on the body; and
   a control system arranged to control the controllable light source system in accordance with the input from the user such that the phototherapeutic illumination is correlated to the force applied by the input of the user.

2. The phototherapy device according to claim 1, wherein the control system is arranged to control the phototherapeutic illumination from the controllable light source system in accordance with said input from the user so as to spatially adapt the phototherapeutic illumination to the spatial position on the body input by the user.

3. The phototherapy device according to claim 1, wherein the control system is arranged to control the controllable light source system so as to change at least one parameter of the phototherapeutic illumination in response to the spatial position on the body input by the user.

4. The phototherapy device according to claim 3, wherein said at least one parameter comprises at least one of: illumination light duration, illumination light intensity, illumination light wavelength, illumination light pulsation width, and illumination light pulsation frequency.

5. The phototherapy device according to claim 1, wherein the input from the user is configured to be processed in accordance with a control algorithm, so as to translate the input from the user into a spatial illumination pattern, and wherein the control system is arranged to spatially control the controllable light source system accordingly.

6. The phototherapy device according to claim 1, wherein the user interface is arranged to allow a user to enter an indication of pain intensity, and to adapt at least one parameter of the phototherapeutic illumination in response thereto.

7. The phototherapy device according to claim 1, wherein the controllable light source system comprises a plurality of individually controllable light sources arranged at respective spatially different zones relative to the patch structure.

8. The phototherapy device according to claim 7, wherein the control system is arranged to activate a limited number of the individually controllable light sources in response to the input from the user so as to allow phototherapeutic illumination for nociceptive pain relief of the body part where the user feels pain.

9. The phototherapy device according to claim 1, wherein the controllable light source system comprises at least one light source arranged to provide light with at least one wavelength within the range 430-480 nm.

10. The phototherapy device according to claim 1, wherein the controllable light source system comprises a plurality of Light Emitting Diodes.

11. A computer executable program code stored on a non-transitory computer readable storage medium to perform a method when executed by a processor system, for controlling a phototherapy device for relieving nociceptive pain of a body part of a user by illumination of at least a part of the body part, wherein the phototherapy device comprises a patch structure arranged to conform to at least a part of the body part, and at least one light source arranged on the patch structure, the method comprising the steps of:
   receiving an input from the user via a user interface regarding a spatial position on the body, wherein the user interface further comprises a touch sensitive panel arranged on the patch structure, the touch sensitive panel being arranged on the opposite side to the side conforming to the at least a part of the body part; and
   controlling the at least one light source arranged on the patch structure in accordance with the input from the user.

* * * * *